(12) United States Patent
Yasumoto

(10) Patent No.: US 6,288,554 B1
(45) Date of Patent: *Sep. 11, 2001

(54) METHOD FOR INSPECTING HERMETICALLY SEALED PACKAGE

(75) Inventor: Kenji Yasumoto, Toyonaka (JP)

(73) Assignee: Joven Denki Kabushiki Kaisha, Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/104,141

(22) Filed: Jun. 24, 1998

Related U.S. Application Data

(63) Continuation-in-part of application No. 08/782,599, filed on Jan. 13, 1997, now abandoned.

(30) Foreign Application Priority Data

Feb. 16, 1996 (JP) .......................................... 8-53816
May 21, 1998 (JP) ................................... 10-158569

(51) Int. Cl.$^7$ .................................................. G01R 31/12
(52) U.S. Cl. .......................................... 324/558; 324/71.1
(58) Field of Search ................................... 324/557, 558, 324/559, 519, 527, 528, 551, 71.1, 72; 73/52, 40, 49.2, 49.3

(56) References Cited

U.S. PATENT DOCUMENTS

| 3,199,023 | * | 8/1965 | Bhimani | 324/551 |
| 4,125,805 | * | 11/1978 | Nagamatsu et al. | 324/558 |
| 4,243,932 | * | 1/1981 | Kakumoto et al. | 324/557 |
| 4,620,145 | * | 10/1986 | Dietz et al. | 324/519 |
| 4,914,395 | * | 4/1990 | Hamamda | 324/557 |

FOREIGN PATENT DOCUMENTS

S50-6998 3/1975 (JP) .
63-85782 * 4/1988 (JP) ....................................... 324/557

* cited by examiner

Primary Examiner—Safet Metjahic
Assistant Examiner—Vincent Q. Nguyen
(74) Attorney, Agent, or Firm—Koda & Androlia

(57) ABSTRACT

An inspection method for inspecting hermetically sealed packages for pinholes, in which when a hermetically sealed package whose contents such as electrically conductive fluid or powder or food are covered with an electrically insulating film is sandwiched between a pair of electrodes and inspected for pinholes with a high voltage applied thereto, occurrence of operation errors due to the atmosphere such as humidity during the inspection is fully prevented. A hermetically sealed package whose contents such as electrically conductive fluid are covered with an electrically insulating film is placed on a grounded support electrode with a side face portion of the hermetically sealed package in contact therewith, and a DC high voltage is applied between the support electrode and an electrode put into close contact with an inspection-object end portion of the hermetically sealed package where pinholes are most likely to occur. As a result, a capacitor formed between the contents 1 and the support electrode is electrically charged. Next, the electrode put into contact with the inspection-object end portion is grounded, and a discharge current from the inspection-object end portion that will flow only when a pinhole is present is detected with a discharge current detecting device, by which the presence or absence of pinholes is detected by the presence or absence of the discharge current.

2 Claims, 3 Drawing Sheets

(A)

(B)

(Temperature, Humidity and Air Pressure
During Test: 21C, 64%, 1010hPa)

METHOD FOR INSPECTING HERMETICALLY SEALED PACKAGE

This is a continuation-in-part of application Ser. No. 08/782,599, filed Jan. 13, 1997, abandoned

BACKGROUND OF THE INVENTION

1. Field of the Invention

The present invention relates to a method for inspecting completely sealed packages, such as food and medical consumption articles, for any pinholes.

2. Prior Art

Today, sealed packaging is used for packing a variety of commodities in addition to food and medical consumption articles such as physiological saline to keep their contents in a sterilized state. In the case of food, the presence of pinholes would cause the contents of the package to contact the air, resulting in deterioration or rot. Also, in the case of medical consumption articles, for example, transfusion bottles, the presence of pinholes would cause contamination or deterioration. Thus, the pinhole inspection for these hermetically sealed packages is of great importance. Conventionally, this pinhole inspection would be carried out in the following method. That is, because a hermetically sealed package does not allow an electrode to be penetrated thereinto, for example in the case of food, a metal pin is stuck into a completed package and taken as one electrode so as to serve as an opposed electrode to an external electrode set in contact with the package. In this state, with a high voltage applied between the two electrodes, the hermetically sealed package is inspected for pinholes, and after the inspection, any pinholes are sealed in a different process. However, this inspection method has had a drawback that the inspection process would be complicated, requiring a subsequent process after the closing of the pinholes. A method for pinhole inspection which solves this drawback and which allows a pinhole inspection to be done without damaging the completed hermetically sealed package has been disclosed in, for example, Japanese Patent Application Publication (Kokoku) No. S50-6998. In this method, a food sealed by a package made from an electrically insulating film is sandwiched between a pair of electrodes, and a voltage is applied between both electrodes so as to give a large difference between capacitances that are formed between the individual electrodes and the food, respectively. Then, a current which is generated by a spark between one of the electrodes and the food is detected, by which any pinhole is detected.

When the presence or absence of any pinhole is detected by detecting a current generated by a spark as described above, it would be the actual case in terms of practical work that the presence or absence of pinholes is detected by a change (magnitude) of the detected current. In this case, applying a voltage between the two electrodes that sandwich the hermetically sealed package would cause a leakage current or charging current to necessarily flow regardless of the presence or absence of pinholes. This phenomenon is more likely to occur particularly with higher voltage, and is also affected by weather such as humidity and temperature of the periphery of the inspection object, which forms the atmosphere during the inspection, where the leakage current becomes larger under the conditions of rain or high humidity. Further, there may arise an error to the current at the detection point due to some influence of floating fine dusts or the like. As a result, the decision as to the presence or absence of pinholes by the magnitude of the current could not be free from operation errors such as a decision of the presence of a pinhole notwithstanding the absence of any pinhole.

The present applicant has previously proposed in Japanese Patent Application No. H8-531816 (U.S. patent application Ser. No. 08/782,599, abandoned) an inspection method for a hermetically sealed package which is fully prevented from occurrence of operation errors due to the atmosphere during the pinhole inspection of a hermetically sealed package in which contents such as electrically conductive fluid or powder or food are covered with an electrically insulating film, where the inspection is done by sandwiching the hermetically sealed package between a pair of electrodes and applying a high voltage between the electrodes.

In this proposal, the hermetically sealed package is placed on a support electrode of a specified configuration, such as a grounded electrode plate, with side face portion of the hermetically sealed package put into contact with the support electrode, and a DC high voltage is applied between the support electrode and an electrode put into close contact with or opposed proximity to an inspection-object end portion of the hermetically sealed package so that the contents of the hermetically sealed package are electrically charged. Then, the grounding of the support electrode is released and moreover the electrode put into contact with the inspection-object end portion is grounded, where a discharge current from the inspection-object end portion is detected, by which any pinhole of the hermetically sealed package is detected.

The above method proposed by the present applicant made it possible to confirm the detection of any pinholes of the hermetically sealed package. However, this pinhole detection method would require a sequence of inspection procedure, including such troublesome steps as releasing the grounding of the support electrode or replacing the support electrode with another support electrode made of insulating material.

SUMMARY OF THE INVENTION

The present invention has been accomplished in view of these and other issues.

An object of the present invention is to provide a method for inspecting hermetically sealed packages which is fully prevented from occurrence of operation errors due to the atmosphere during the inspection with a simpler procedure.

For this method, the hermetically sealed package to be inspected can be exemplified, in the field of food, principally by cylindrical-shaped packages such as sausage sealed and packaged in unit pieces, and besides retort foods packed in a flat bag made of plastic film. In the field of medical consumption articles, the hermetically sealed package can be exemplified by blood preparations such as transfusion blood and blood plasmas contained in a thin plastic bag in addition to transfusion agents such as physiological saline or Ringer's solution contained in a transfusion bottle also made of thin plastic as the inspection object for prevention of contamination and deterioration of the contents due to contact with outside air via pinholes.

Furthermore, hermetically sealed packages in which a powder conductive material such as cooked rice or solid-matter iron powder is sealed in a thin plastic bag also can be an object of inspection as well.

In order to achieve the above object, the present inventors have reached the present invention by finding out, as a result of discussions through energetic experiments that the step of releasing the grounding of the support electrode for the hermetically sealed package in the procedure of the above-described method can be omitted. That is, a method for inspecting hermetically sealed packages according to the present invention comprises the steps of: placing a hermetically sealed package, in which contents such as electrically conductive fluid or powder or food are covered with an electrically insulating film, on a support electrode of a specified configuration such as a grounded electrode plate with a side face portion of the hermetically sealed package brought into contact therewith; applying a DC high voltage between the support electrode and an electrode, which is put into close contact with or opposed proximity to an inspection-object end portion of the hermetically sealed package, so that a capacitor formed between the electrically conductive contents and the support electrode via the electrically insulating film is electrically charged; grounding the electrode put into contact with the inspection-object end portion; and detecting a discharge current from the inspection-object end portion so as to detect any pinhole of the hermetically sealed package. In this method, the electrode may be of electrically conductive liquid or electrically conductive gel.

DETAILED DESCRIPTION OF THE INVENTION

Figure 1:
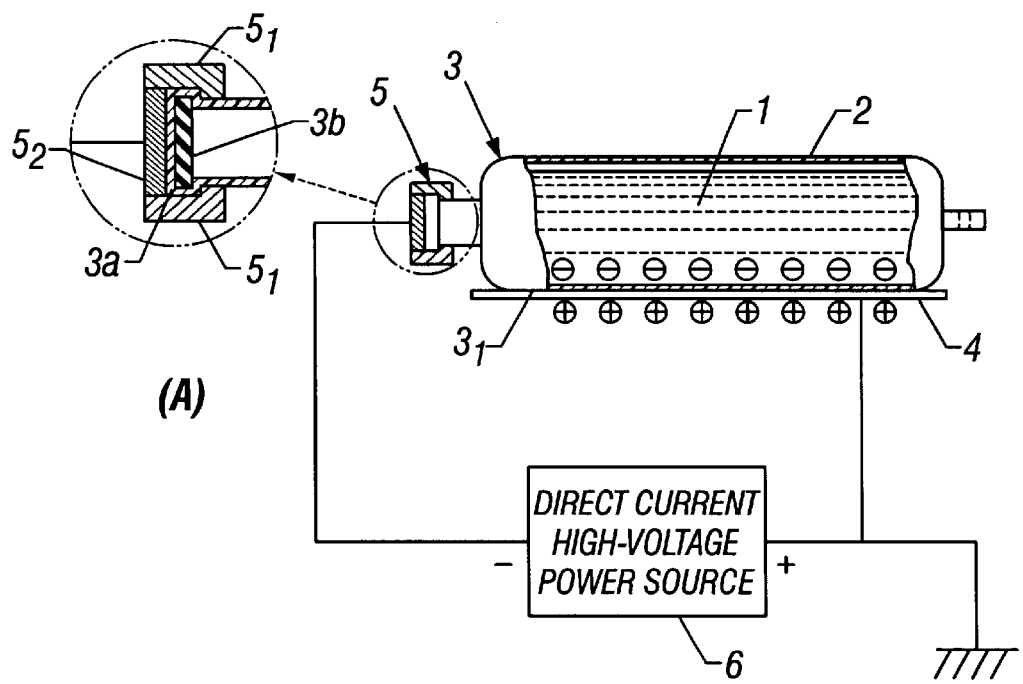
FIG. 1 is an arrangement diagram of an inspection method of the present invention in the case where the hermetically sealed package is a transfusion bottle for physiological saline.
Figure 1:
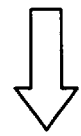

The method for inspecting hermetically sealed packages according to the present invention comprises the steps of: placing a hermetically sealed package 3, in which contents 1 such as electrically conductive fluid or powder or food are covered with an electrically insulating film 2, on a support electrode 4 of a specified configuration such as a grounded electrode plate with a side face portion $3_1$ of the hermetically sealed package 3 brought into contact therewith; applying a DC high voltage between the support electrode 4 and an electrode 5, which is put into close contact with or opposed proximity to an inspection-object end portion 3a of the hermetically sealed package 3, so that a capacitor formed between the electrically conductive contents 1 and the support electrode 4 via the electrically insulating film 2 is electrically charged; then grounding the electrode 5 put into contact with the inspection-object end portion 3a; and detecting a discharge current from the inspection-object end portion 3a so as to detect any pinhole of the hermetically sealed package 3. In this method, the electrode 5 may be of electrically conductive liquid or electrically conductive gel.

With such a method, in the case where a pinhole is present at the inspection-object end portion 3a of the hermetically sealed package 3, when the DC voltage is applied between the electrode 5 put into close contact with or opposed proximity to the inspection-object end portion 3a of the hermetically sealed package 3 and the side face portion $3_1$ of the hermetically sealed package 3, a capacitor is formed by taking the electrically conductive contents 1 of the hermetically sealed package and the support electrode 4 as electrodes, and by taking the electrically insulating film 2 as a dielectric. Therefore, negative (−) charges occur to the electrically conductive contents 1 through the pinhole via the electrically insulating film 2 making contact with the support electrode 4, relative to positive (+) charges of the grounded support electrode, so that electricity is charged between the contents 1 and the support electrode 4. In addition, when the inspection-object end portion 3a and the electrode 5 are in opposed proximity to each other, a spark due to the DC high voltage occurs between the electrode 5 and the pinhole of the inspection-object end portion, so that electricity is charged between the contents 1 of the hermetically sealed package and the support electrode 4.

Next, the electrode 5 put into contact with the inspection-object end portion 3a (if in opposed proximity to each other, they are put into contact) is grounded, so that the electric charges accumulated in the contents 1 are discharged via the pinhole. This discharge current is detected, by which the pinhole at the inspection-object end portion 3a is detected. In this process, the discharge current could not be detected without the presence of a pinhole at the inspection-object end portion.

In this detection, any pinhole can be detected without errors, irrespective of the atmosphere during the inspection, where the decision is made not by any change (magnitude) of the charged current but by the presence or absence of a discharge current due to the presence or absence of a pinhole at the inspection-object end portion 3a (where pinholes are most likely to occur).

Furthermore, as the electrode 5, electrically conductive rubber or electrically conductive plastic formed so that the electrode 5 can be put into close contact with the inspection-object end portion 3a may be used. That is, in the case where the inspection-object end portion 3a is provided by a die-molding product of mass production used for the inspection-object end portion 3a, on in other like cases, the inspection-object end portion 3a maintains constant or generally constant in shape, so that the electrode 5 can be easily put into close contact with the surface of the inspection-object end portion by taking advantage of the elasticity of this electrically conductive rubber or electrically conductive plastic.

In the present invention, the electrically insulating film 2 with which the electrically conductive contents 1 of the hermetically sealed package 3 to be inspected are covered may be plastic film or thin-walled plastic matching the contents 1.

More specifically, when the contents 1 are fish sausage as an example, a bag made of vinylidene chloride is used. After minced meat of fish sausage is filled in the beg, the bag is clipped at both ends by aluminum wire and subjected to retort sterilization. Further, even retort foods employing a bag of composite film (laminate film) containing no aluminum foils in their internal layers can be the objective hermetically sealed package to be inspected. In this case, bags of a composite film made of nylon and polypropylene, polyester and polypropylene, or polyester and vinylidene chloride and polypropylene are used. On the other hand, in the case of transfusions such as physiological saline and Ringer's solution, transfusion bottles of a thin plastic specified for individual cases are used.

Furthermore, the contents 1 may be a fluid of a solid matter, such as iron powder or other electrically conductive powder, as the electrically conductive fluid.

The support electrode 4 on which the hermetically sealed package 3 is to be placed may be of any shape which should be determined depending on the form of the side face portion $3_1$ at which the hermetically sealed package 3 is placed in contact on the support electrode 4, where the support electrode 4 may be a flat plate-shaped electrode, or an electrode whose upper contact surface is planar shaped with many rollers of small diameter located adjacent to one another, or an electrode having a circular inner surface so that the cross section of the electrode corresponds to the circular sausage or the like. Also, the electrode 5 to be put into close contact with or opposed proximity to the inspection-object end portion 3a may be a metallic one, and further may be ones made of electrically conductive rubber (porous conductive rubber) or electrically conductive plastic formed so that the electrode 5 can be put into close contact with the inspection-object end portion 3a. For the detection of a discharge current from the inspection-object end portion 3a, a current transformer (CT) of such a type that its detection portion is wound around a lead wire through which the discharge current flows, or a current detecting device (residual charge detector) connected in series to the lead wire may be used. Furthermore, the discharge current can be measured by inputting to an oscilloscope an output of a current probe through which the lead wire is passed.

EMBODIMENTS

Embodiment 1

FIG. 1 shows a case where the hermetically sealed package 3 is a transfusion bottle for use in instillation in which physiological saline is sealed.

The transfusion bottle 3 has a body portion formed of a rather thick plastic film 2 with a cross section formed into a rounded 65 mm×90 mm rectangular shape having a height of 240 mm, and a content volume of 1000 milliliters. The inspection-object end portion 3a of the hermetically sealed package 3 where pinholes are liable to occur is one formed in such a way that a rubber stopper portion 3b for insertion of an instillation needle is provided airtight at an opening of a stepped end portion having an outer diameter of 28 mm and a thickness of 8 mm while a hanging ring portion is provided on the opposite side. Places in this inspection-object end portion 3a where pinholes or gaps equivalent to pinholes are liable to occur are peripheries of the ring-shaped stepped portion at which the rubber stopper portion 3b is held, and the boundary portion between the rubber stopper portion 3b and the opening of the stepped portion at which the rubber stopper portion 3b is held.

In order to inspect the inspection-object end portion 3a of this transfusion bottle 3 for pinholes, at a first step, a DC high voltage is applied between the electrode 5 put into close contact with the inspection-object end portion 3a, and the support electrode 4 on which the side face portion $3_1$ of the transfusion bottle 3 is placed in contact therewith. The electrode 5 to be put into close contact with the inspection-object end portion 3a is composed of a metallic ring portion comprising two-divided portions $5_1$ having a specified cross-sectional shape, and a metallic tablet portion $5_2$ of a specified cross section which is so formed as to be fit into the ring portion in close contact with a front surface of the rubber stopper portion 3b. The electrode 5 is put into use by bringing the two-divided portions $5_1$ and the tablet portion $5_2$ into close contact with the inspection-object end portion 3a from both sides and front side, respectively.

On the other hand, the support electrode 4 on which the transfusion bottle 3 is to be placed has a flat plate-like shape of specified dimensions to support the overall side face portion $3_1$ of the transfusion bottle 3. A bottom part of the electrode 4 is grounded via a lead wire and is connected to the positive (+) side of DC high voltage power source 6. Furthermore, the electrode 5 brought into close contact with the inspection-object end portion 3a is connected to the negative (−) side of the DC high voltage power source 6, and then a specified DC high voltage (0.6 kV to 30 kV) is applied between the electrode 5 and the support electrode 4. As a result, a capacitor formed between the electrically conductive contents 1 and the support electrode 4 via the electrically insulating film 2 is electrically charged.

Next, the connection of the electrode 5 to the negative (−) side of the DC high voltage power source 6 on the inspection-object end portion 3a side is released, and the lead wire 8 from the electrode 5 is grounded. This lead wire 8 is additionally equipped with a discharge current detecting device 7 having a current detecting portion 7a surrounding the lead wire 8 purposed for the detection of a current flowing through the lead wire 8. The discharge current detecting device 7 may be a specified current transformer (CT), whereas a current detecting device connected in series between the electrode 5 and the grounding may also be used for the detection of current. Furthermore, a discharge current can be detected and measured by inputting to an oscilloscope an output of a current probe penetrated through the lead wire 8.

With this arrangement, when a pinhole is present in the inspection-object end portion 3a, a discharge current flows through the lead wire 8 because the capacitor formed between the contents 1 of the hermetically sealed package 3 and the support electrode 4 has been electrically charged, allowing the discharge current detecting device 7 to detect the resulting discharge current. When there are no pinholes, the discharge current detecting device 7 does not detect the discharge current. Accordingly, by using this current detection output to make a display with some appropriate display means such as a meter, an alarm buzzer or an alarm lamp, the presence or absence of pinholes at the inspection-object end portion 3a can be known with ease.

Figure 4:
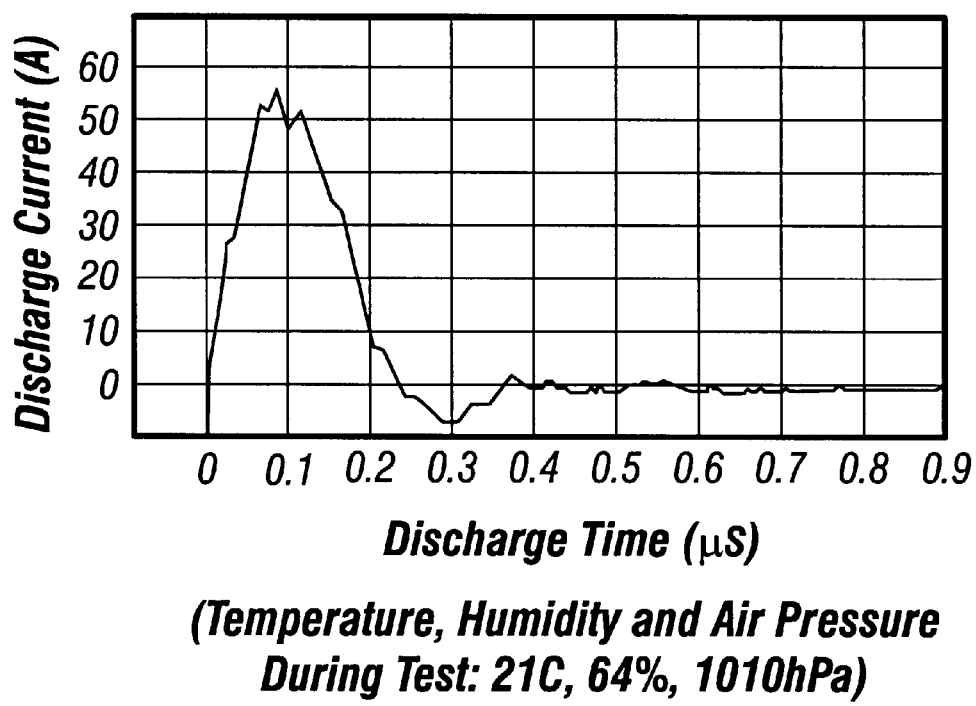
FIG. 4 is a graph of a discharge current in the case where pinholes are present in the physiological saline.

FIG. 4 is a graph attached to a report, dated Apr. 10, 1998 as a result of a test conducted at Osaka Sangyo Gijutsu Sogo Kenkyujo (Technology Research Institute of Osaka Prefecture), which is an official testing facility, in which the inspection method for hermetically sealed packages of the present invention was tested with physiological saline containers, the graph showing a discharge current resulting when electric charges accumulated on the pinholeinspection object are discharged.

More specifically, the graph shows a time chart of a discharge current measured in the above-described test, where with the physiological saline container placed on an aluminum-plate support electrode, a 20 kV voltage was applied from the DC high voltage power source via the test member, and afterwards the lead wire derived from the inspection-object test member was grounded via a residual charge detector and then the current flowing therethrough was measured by using a current probe and an oscilloscope.

As is apparent from the chart, the discharge current is instantaneous (with a crest portion of about 0.25 :s), the current peak value measuring 55 amperes. In addition to this, although not shown, a mayonnaise container and a ketchup container were also tested likewise, and the discharge current showed similar tendencies. The current peak value was 30A with the mayonnaise container, and 28A with the ketchup container, the discharge time being about 1.5 :s in crest portion in both cases. In addition, the report describes "these tests confirmed that electric charges were accumulated through a pinhole and afterwards discharged through the pinhole."

Embodiment 2

Figure 2:
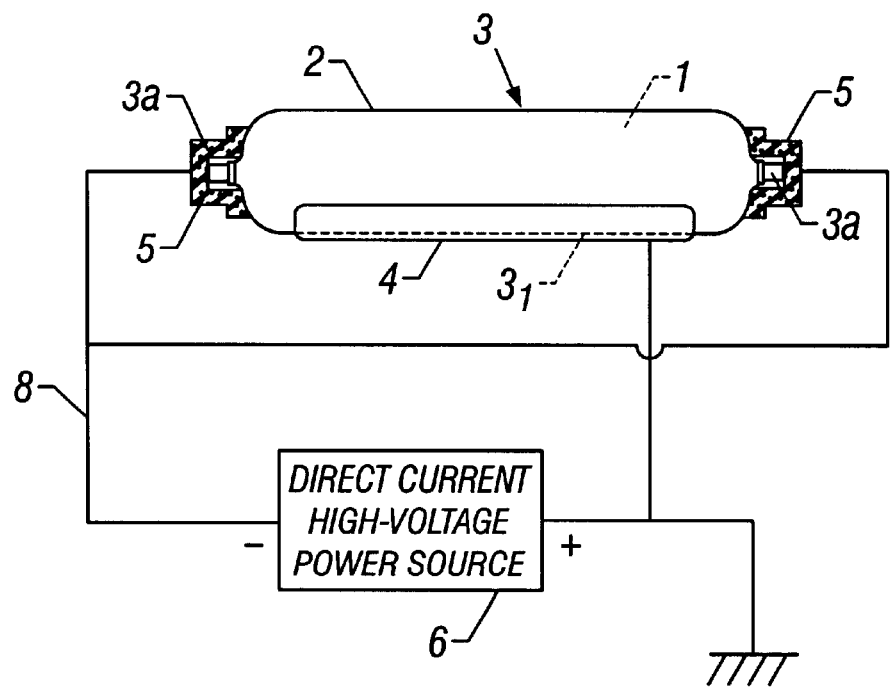
FIG. 2 is an arrangement diagram showing a pre-stage of the inspection method according to the invention in the case where the hermetically sealed package is a sausage with both ends tightly bound.

FIG. 2 shows a case in which a DC high voltage is applied to an inspection object, where the inspection-object end portion 3a of the hermetically sealed package 3 is a tightly binding portion of a bag in which contents 1 are sealed with an electrically insulating film 2. In this case, pinholes which may occur to the electrically insulating film 2 will be concentrated around this inspection-object end portion 3a.

The contents 1 are, for example, fish sausage or the like. As the electrically insulating film 2, a single-substance film of vinylidene chloride is used by virtue of its transparency and superior contractility and barrier property, and the end portion of the bag which is filled with the contents is tightly bound with aluminum wire. As the support electrode 4 on which the end portion of the bag is to be placed, a metal plate of a specified shape with its inner surface formed into a circular-arc shape in correspondence to the inspection object is used. The electrodes 5 to be put into close contact with the inspection-object end portions 3a on both ends, which are tightly binding portions, are each made of porous conductive rubber, and recessed portions that can accommodate the inspection-object end portions 3a are provided on one side face in central part of the electrodes 5, the recessed portions being formed into a cap-like shape so as to make close contact with the inspection-object end portions 3a by being pushed into the end portions 3a. The support electrode 4 is grounded, and the positive (+) side of the DC high voltage power source 6 is connected to the support electrode 4 while a pair of cap-like electrodes 5 on both ends of the inspection object are connected to the negative (−) side of the DC high voltage power source 6, in which state a DC high voltage of 0.6 kV to 30 kV is applied between the support electrode 4 and the electrodes 5 overlaid on the inspection-object end portions 3a, as in the foregoing Embodiment 1. As a result, a capacitor formed between the electrically conductive contents 1 and the support electrode 4 via the electrically insulating film 2 is charged. Therefore, the lead wire 8 derived from the pair of electrodes 5 is released from the connection on the negative (−) side of the DC high voltage power source 6, and grounded for the detection of a discharge current.

Then, by detecting the discharge current that flows through the lead wire 8 when a pinhole is present at the inspection-object end portion 3a, with a discharge current detecting device 7 such as a current transformer (CT) as in the foregoing Embodiment 1, the presence or absence of pinholes in the inspected hermetically sealed package 3 can be detected depending on the presence or absence of the discharge current.

Embodiment 3

Figure 3:
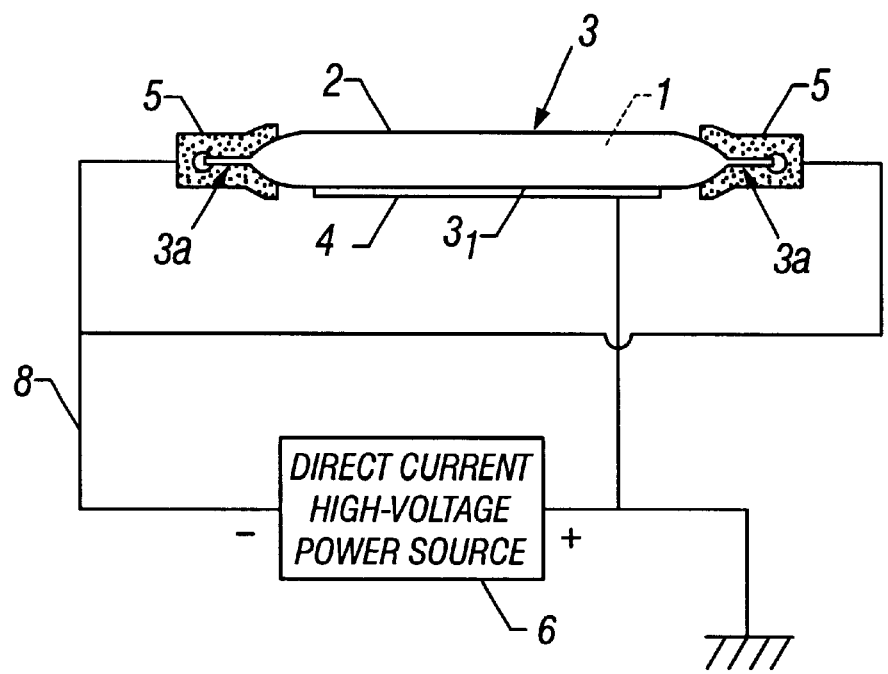
FIG. 3 is a schematic view showing a pre-stage of the inspection method according to the invention in the case where the hermetically sealed package is food contained in a heat sealed bag such as retort food or the like which is heat sealed.

FIG. 3 shows a case where a hermetically sealed package 3, such as retort food, in which each inspection-object end portion 3a is a heat sealed portion of a bag made of plastic film is inspected. In such hermetically sealed packages, pinholes which may occur to the electrically insulating film will be concentrated around inspection-object end portions 3a that are heat sealed portions.

The electrically conductive contents 1 are food contained in a bag such as retort food. As the electrically insulating film 2, the above-described composite plastic film (laminate film) containing no aluminum foil in its inner layer is used. The hermetically sealed package is placed on a flat plate-like support electrode 4 corresponding to the size of the inspection object, and the support electrode 4 is grounded via a lead wire and besides connected to the positive (+) side of the DC high voltage power source 6. In the electrode 5 to be put into close contact with each inspection-object end portion 3a, a slit of such a specified shape as to be able to pinch the inspection-object end portion 3a is provided on one side on the center line made of porous conductive rubber, and with both sides of the slit opened, the inspection-object end portion 3a is inserted into the slit so as to be pinched therebetween. The inspection-object end portions 3a, which are heat sealed portions on both sides of the hermetically sealed package 3, are pinched by the electrodes 5 in close contact therewith, respectively, and connected to the negative (−) side of the DC high voltage power source 6. Then, a DC high voltage of 0.6 kV to 30 kV is applied between the support electrode 4 and the electrodes 5 put into close contact with the inspection-object end portion 3a. After that, the lead wire 8 derived from the pair of electrodes 5 is released from the connection on the negative (−) side of the DC high voltage power source 6 and then grounded, where a discharge current flowing through the grounded lead wire 8 is detected with the discharge current detecting device as in the foregoing Embodiment. By detecting this discharge current, the presence or absence of any pinholes in the vicinity of the heat sealed portions of the hermetically sealed package 3 where pinholes are most likely to occur can be detected.

As described above, in the process of electrically charging the inspection-object hermetically sealed package and performing the inspection by detecting a resultant discharge current, because the discharge current cannot be detected without the presence of pinholes at the inspection-object portion, any pinholes can be detected without errors independently of the atmosphere during the inspection.

In the above Embodiments, it has been arranged that the support electrode is set to the positive (+) side and the electrode on the inspection-object side is set to the negative (−) side for the application of a DC high voltage to the inspection-object hermetically sealed package. However, the settings of positive (+) and negative (−) sides may also be inverted depending on the contents of the inspection-object package.

Furthermore, in addition to the above-described Embodiments, the method for inspecting hermetically sealed packages according to the present invention can be applied to injection solutions or ampoules for drench. For example, the main body portion of an ampoule is placed on the support electrode having a circular-arc shaped inner surface, and an electrode is overlaid on an end portion of the ampoule including a neck portion where pinholes are liable to occur. Then, after a DC high voltage is applied between the electrode and the support electrode, a discharge current from the ampoule is detected, by which an inspection for any pinholes can be achieved. Thus, the inspection method of the present invention can afford a wide variety of pinhole inspection.

As described above, according to the method for inspecting hermetically sealed packages of the present invention, in the pinhole inspection of a hermetically sealed package in which contents such as electrically conductive fluid or powder or food is covered with an electrically conductive film, a capacitor formed between the inspection-object hermetically sealed package and the support electrode is electrically charged, and a discharge current is detected only when a pinhole is present, by which any pinhole is detected. With this arrangement, the hermetically sealed package can be inspected for the presence or absence of pinholes effectively, in combination with the inspection of the inspection-object end portion at a site where pinholes are most likely to occur, without being affected by the atmosphere during the inspection such as humidity or floating fine dusts, as would conventionally be involved in the pinhole detection by the magnitude of the current flowing through the inspection object with a high voltage applied thereto, and by fully preventing the occurrence of operation errors.

Furthermore, according to the present invention, when the inspection-object end portion of a hermetically sealed package where pinholes are most likely to occur is constant in shape because of mass production, the electrode made of electrically conductive rubber or electrically conductive plastic is put into contact with the inspection-object end portion by using its elasticity so that the hermetically sealed package can be easily inspected.

What is claimed is:

1. A method for inspecting hermetically sealed packages, consisting of the ordered steps of:

placing a hermetically sealed package, in which contents consisting of electrically conductive food products are covered with an electrically insulating film, on a support electrode comprising a grounded electrode plate with a side face portion of the hermetically sealed package brought into contact therewith;

applying a DC high voltage between the support electrode and a contact electrode which is contacted with an inspection end portion of the hermetically sealed package, so that a capacitor formed between the electrically conductive contents and the support electrode via the electrically insulating film is electrically charged;

disconnecting the DC high voltage from the contact electrode;

connecting the contact electrode which is in contact with the inspection end portion to ground; and detecting a discharge current from the inspection end portion to detect any pinhole in the hermetically sealed package.

2. The inspection method for hermetically sealed packages according to claim 1, wherein the contact electrode is made of electrically conductive rubber formed so that the electrode can be contacted with the inspection end portion.

* * * * *